(12) United States Patent
Umezawa

(10) Patent No.: US 10,492,694 B2
(45) Date of Patent: Dec. 3, 2019

(54) OBJECT INFORMATION ACQUISITION APPARATUS

(71) Applicant: CANON KABUSHIKI KAISHA, Tokyo (JP)

(72) Inventor: Kohtaro Umezawa, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 159 days.

(21) Appl. No.: 15/242,785

(22) Filed: Aug. 22, 2016

(65) Prior Publication Data

US 2017/0055843 A1    Mar. 2, 2017

(30) Foreign Application Priority Data

Aug. 27, 2015  (JP) .................................. 2015-168247
Jul. 26, 2016  (JP) .................................. 2016-146655

(51) Int. Cl.
| | | |
|---|---|---|
| A61B 5/00 | (2006.01) | |
| A61B 6/04 | (2006.01) | |
| A61B 6/00 | (2006.01) | |
| A61B 8/08 | (2006.01) | |
| A61B 8/00 | (2006.01) | |

(52) U.S. Cl.
CPC .......... *A61B 5/0095* (2013.01); *A61B 5/0091* (2013.01); *A61B 5/684* (2013.01); *A61B 5/708* (2013.01); *A61B 5/744* (2013.01); *A61B 6/0435* (2013.01); *A61B 6/4417* (2013.01); *A61B 6/502* (2013.01); *A61B 8/0825* (2013.01); *A61B 8/406* (2013.01); *A61B 8/4263* (2013.01)

(58) Field of Classification Search
None
See application file for complete search history.

(56) References Cited

U.S. PATENT DOCUMENTS

| | | | |
|---|---|---|---|
| 2013/0217995 A1 | 8/2013 | Kruger | 600/407 |
| 2013/0312526 A1 | 11/2013 | Oishi | 73/620 |
| 2014/0051969 A1* | 2/2014 | Suzuki | A61B 5/0095 600/407 |
| 2014/0316236 A1 | 10/2014 | Umezawa | 600/407 |
| 2014/0350358 A1* | 11/2014 | Oikawa | A61B 5/743 600/301 |

(Continued)

FOREIGN PATENT DOCUMENTS

JP    2012-179348 A    9/2012

*Primary Examiner* — Joel F Brutus
(74) *Attorney, Agent, or Firm* — Venable LLP

(57) ABSTRACT

An object information acquisition apparatus, comprises a holding member that holds an object and to be movable relative to the object; a position acquirer that acquires information on a position of the object; a first controller that controls a position of the holding member; a measurement unit that receives acoustic waves from the object; a second controller that controls a position of the measurement unit; an information acquirer that acquires information of the object; and a storage unit that stores history information representing information on a contact state of the holding member with the object, wherein the first controller controls the position of the holding member independently of the control performed by the second controller and adjusts the contact state of the holding member with the object based on the history information.

19 Claims, 12 Drawing Sheets

(56) References Cited

U.S. PATENT DOCUMENTS

| | | | |
|---|---|---|---|
| 2015/0031998 A1* | 1/2015 | Kyono | A61B 8/4281 600/437 |
| 2015/0119680 A1* | 4/2015 | Tanaka | A61B 5/708 600/407 |
| 2015/0228093 A1* | 8/2015 | Miyasa | G06T 11/60 382/131 |

* cited by examiner

OBJECT INFORMATION ACQUISITION APPARATUS

BACKGROUND OF THE INVENTION

Field of the Invention

The present invention relates to an object information acquisition apparatus that acquires information on the inside of an object.

Description of the Related Art

In recent years, studies for imaging shape information or physiological information, i.e., functional information on the inside of objects have been pursued in the medical field. As one of such technologies, photoacoustic tomography (PAT) has been proposed recently.

When light such as pulse laser light is irradiated onto a living body serving as an object, acoustic waves (typically ultrasonic waves) are generated while the light is absorbed into living-body tissues inside the object. This phenomenon is called a photoacoustic effect, and acoustic waves generated by the photoacoustic effect are called photoacoustic waves. Since each of tissues constituting an object has a different light energy absorption rate, the sound pressure of generated photoacoustic waves is also different. In the PAT, generated photoacoustic waves are received by a probe, and received signals are mathematically analyzed. Thus, it is possible to form an image of the distribution of optical characteristic values inside an object.

The distribution of optical characteristic values includes, for example, the distribution of sound pressure generated by light absorption (initial sound pressure distribution) or the distribution of light absorption coefficients. In addition, it is also possible to obtain the concentration-related distribution of substances existing inside an object (the distribution of values related to the concentration of the substances) in such a way that a plurality of pulsed light having mutually different wavelengths is applied to calculate a light absorption coefficient for each wavelength.

When an object greatly moves or deforms during the irradiation of pulsed light, distortion or blurring occurs in acquired image data. The occurrence of the distortion or blurring reduces accuracy in calculating distribution related to acquired optical characteristic values, which causes reduction in the reliability of image data. In order to reduce the distortion or blurring, it is necessary to hold an object so as not to move or deform during measurement.

As a related technology, US Patent Application Publication No. 2013/217995 discloses a photoacoustic apparatus that holds the breast serving as an object by a plastic cup and measures the same.

In addition, Japanese Patent Application Laid-open No. 2012-179348 discloses an apparatus provided with a movement mechanism that moves a cup-shaped holding member relative to an object.

SUMMARY OF THE INVENTION

When an object is held by a cup-shaped holding member, the contact state between the object and the holding member may greatly influence measurement accuracy. For example, when a holding member is a cup-shaped member matching the shape of the breast, the deviation between the center of the cup and the center of the breast causes a nonuniform gap and fluctuations in the characteristics of the transmission path of acoustic waves, which results in reduction in measurement accuracy.

In order to prevent this problem, it is necessary to confirm a holding state of an object and correct the same as occasion demands. For example, according to an apparatus described in US Patent Application Publication No. 2013/217995, it is possible to confirm a position of an inserted object by a camera and readjust the position of the object based on a confirmation result.

However, in the case of an apparatus that performs measurement in a state in which the breast is inserted, there is a case that the readjustment of a position places a burden on an examinee. For example, in the case of an apparatus that performs measurement in a state in which an examinee is in a prone position, it is necessary for the examinee to temporarily sit up and take the prone position again.

On the other hand, according to an apparatus described in Japanese Patent Application Laid-open No. 2012-179348, it is possible to move the holding member to accurately align an object with a holding member.

Meanwhile, there is a case that the same object is measured on another day in order to observe the progression of disease. In this case, it is expected that the comparison between object information is made easier as measurement conditions are close to each other and useful information for an observer is easily obtainable.

The inventions described in US Patent Application Publication No. 2013/217995 and Japanese Patent Application Laid-open No. 2012-179348 have room for an improvement in bringing current measurement conditions of an object close to measurement conditions in the past.

The present invention has been made in view of the above problems and has an object of providing an object information acquisition apparatus capable of bringing current measurement conditions close to measurement conditions in the past while adjusting a holding state of an object.

The present invention in its one aspect provides an object information acquisition apparatus, comprising a holding member configured to come in contact with an inserted object to hold the object and to be movable relative to the object; a position acquisition unit configured to acquire information on a position of the inserted object; a first control unit configured to control a position of the holding member to adjust a contact state of the holding member with the object; a measurement unit configured to receive acoustic waves from an inside of the object and to be movable relative to the object; a second control unit configured to control a position of the measurement unit; an information acquisition unit configured to acquire information on the inside of the object based on the received acoustic waves; and a storage unit configured to store history information representing information on a contact state of the holding member with the object, obtained when the object is measured in a past, wherein the first control unit is configured to control the position of the holding member independently of the control performed by the second control unit and further adjust the contact state of the holding member with the object based on the history information.

The present invention in its another aspect provides an object information acquisition apparatus, comprising a measurement unit configured to receive acoustic waves from an inside of an object; a holding member configured to come in contact with the object to hold the object and to be movable relative to the measurement unit; a position acquisition unit configured to acquire information on a position of the object; a control unit configured to control a position of the holding member to adjust the position of the object; an information acquisition unit configured to acquire information on the inside of the object based on the received acoustic waves;

and a storage unit configured to store history information representing information on a position of the object, obtained when the object is measured in a past, wherein the control unit is configured to adjust a position of the object relative to the measurement unit, based on the history information.

According to an embodiment of the present invention, it is possible to provide an object information acquisition apparatus capable of bringing current measurement conditions close to measurement conditions in the past while adjusting a holding state of an object.

Further features of the present invention will become apparent from the following description of exemplary embodiments with reference to the attached drawings.

DESCRIPTION OF THE EMBODIMENTS

Figure 1:
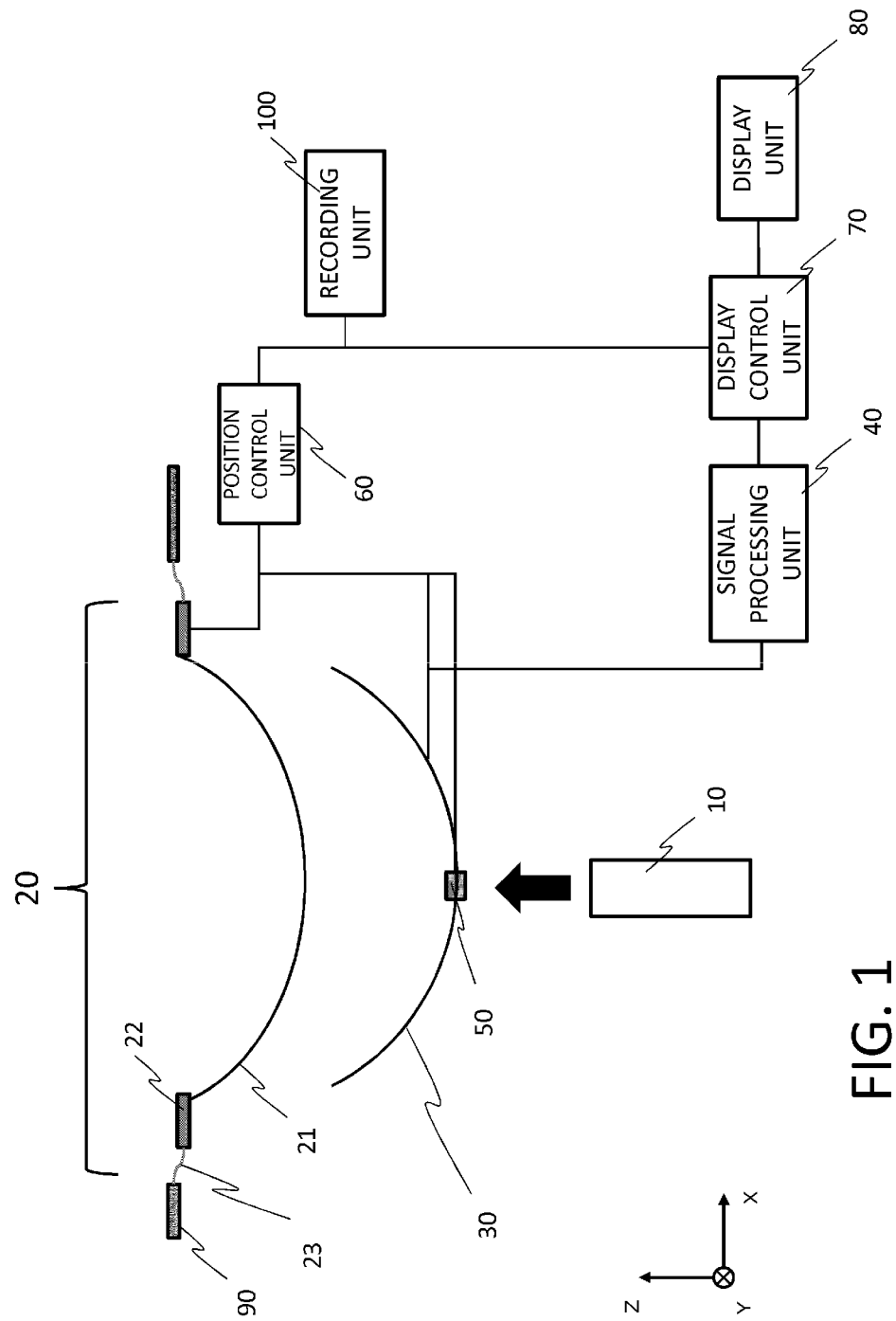
FIG. 1 is a configuration diagram of a photoacoustic measurement apparatus according to a first embodiment.

Hereinafter, a description will be given in detail of embodiments of the present invention with reference to the drawings. Note that the same constituents will be denoted by the same reference symbols in principle and their descriptions will be omitted. In addition, numerical values, materials, detailed apparatus configurations used in the description of the embodiments are only for exemplary purpose and do not intend to limit the scope of the invention.

(First Embodiment)

A photoacoustic measurement apparatus according to a first embodiment is an apparatus that irradiates pulsed light to an object and then receives and analyzes photoacoustic waves generated inside the object due to the pulsed light to form an image of information on optical characteristics inside the object (hereinafter characteristics information).

Note that in the specification, the "photoacoustic waves" indicate acoustic waves generated by the absorption of light and include those called "acoustic waves," "ultrasonic waves," "sound waves," "elastic waves," and "light ultrasonic waves" generated by the absorption of light.

In addition, the "characteristics information" is information reflecting a light energy absorption ratio, and includes the generation source distribution of acoustic waves, initial sound pressure distribution inside an object, light energy absorption density distribution and absorption coefficient distribution derived from the initial sound pressure distribution, concentration information on substances constituting tissues, or the like.

The concentration information on substances is information on the concentration of the substances existing inside an object, which is calculated using characteristics information on a plurality of wavelengths, and includes oxygen saturation degree distribution, total hemoglobin concentration distribution, oxidized hemoglobin concentration distribution, reduced hemoglobin concentration distribution, or the like. Moreover, the concentration information may also include glucose concentration, collagen concentration, melanin concentration, volume fractions of fat and water, or the like. Such information is generated as two-dimensional or three-dimensional distribution data and output as an image.

Note that the photoacoustic measurement apparatus of the embodiment is mainly directed at analyzing cancers or vascular diseases in persons or animals, monitoring chemical treatment over time, or the like. Accordingly, it is assumed that a portion of a living body, specifically, a region (the breast, internal organ, circulatory organ, digestive organ, bone, muscle, fat, or the like) of a person or an animal is to be examined as an object. In addition, a substance to be examined includes hemoglobin, glucose, water, melanin, collagen, lipid, or the like in a living body. Moreover, the substance to be examined includes any substance featuring a light absorption spectrum such as a contrast medium including, e.g., ICG (indocyanine green) administered into the body.

<System Configuration>

FIG. 1 is a configuration diagram of the photoacoustic measurement apparatus according to the first embodiment.

The photoacoustic measurement apparatus according to the first embodiment has a light irradiation unit 10, an object holding unit 20, a probe unit 30 provided with a plurality of acoustic elements, a signal processing unit 40, a state measurement unit 50, a position control unit 60, a display control unit 70, a display unit 80, and a housing 90. Each of the constituents will be described with reference to FIG. 1.

«Light Irradiation Unit 10»

The light irradiation unit 10 is a unit that generates pulsed light and irradiates the same onto an object, and is constituted by a light source and an irradiation optical system.

The light source is desirably a laser light source in order to obtain a large output, but a light-emission diode, a flash lamp, or the like may be used instead of a laser. When a laser is used as the light source, various types such as a solid-state laser, a gas laser, a dye laser, and a semiconductor laser are available.

Ideally, a Ti:Sa laser pumped by a Nd:YAG laser, an optical parametric oscillators (OPO) laser, an alexandrite laser, or the like that produces a large output and is capable of continuously varying a wavelength may be used. In addition, a plurality of short-wavelength lasers having different wavelengths may be used.

The timing, waveform, intensity, or the like of the irradiation is controlled by a light source control unit not shown. The light source control unit may be integrated with the light source.

In addition, a wavelength of pulsed light is desirably a specific wavelength to be absorbed by a specific component among those constituting an object, and is a wavelength at which the light propagates through the inside of the object.

Specifically, when an object is a living body, the wavelength is greater than or equal to 400 nm and less than or equal to 1600 nm.

Particularly, when an image of a depth portion of a living body is formed, light at a wavelength band called the "biological window" that is less absorbed by the background tissues of the living body may be used. Specifically, a wavelength band of greater than or equal to 700 nm and less than or equal to 1100 nm is preferable. On the other hand, when an image of blood vessels near the front surface of a living body is formed at high resolution, a visible light region is preferably used. However, it is also possible to use the regions of terahertz waves, micro waves, and radio waves.

In addition, in order to effectively generate photoacoustic waves, it is necessary to apply light in a substantially short period of time according to the heat characteristics of an object. When an object is a living body, a pulse width of pulsed light generated from the light source is preferably in the range of about 1 to 100 nanoseconds.

Note that pulsed light generated from the light irradiation unit is preferably introduced into an object by a light propagation member (optical member) such as an optical fiber, a lens, a mirror, and a diffusion plate. In addition, during the introduction of pulsed light, a spot shape or light density of the pulsed light may be changed using such an optical member. In the embodiment, pulsed light generated from the light irradiation unit 10 is irradiated onto an object via an opening provided at the bottom surface of the probe unit 30 that will be described later.

«Object Holding Unit 20»

Figure 7:
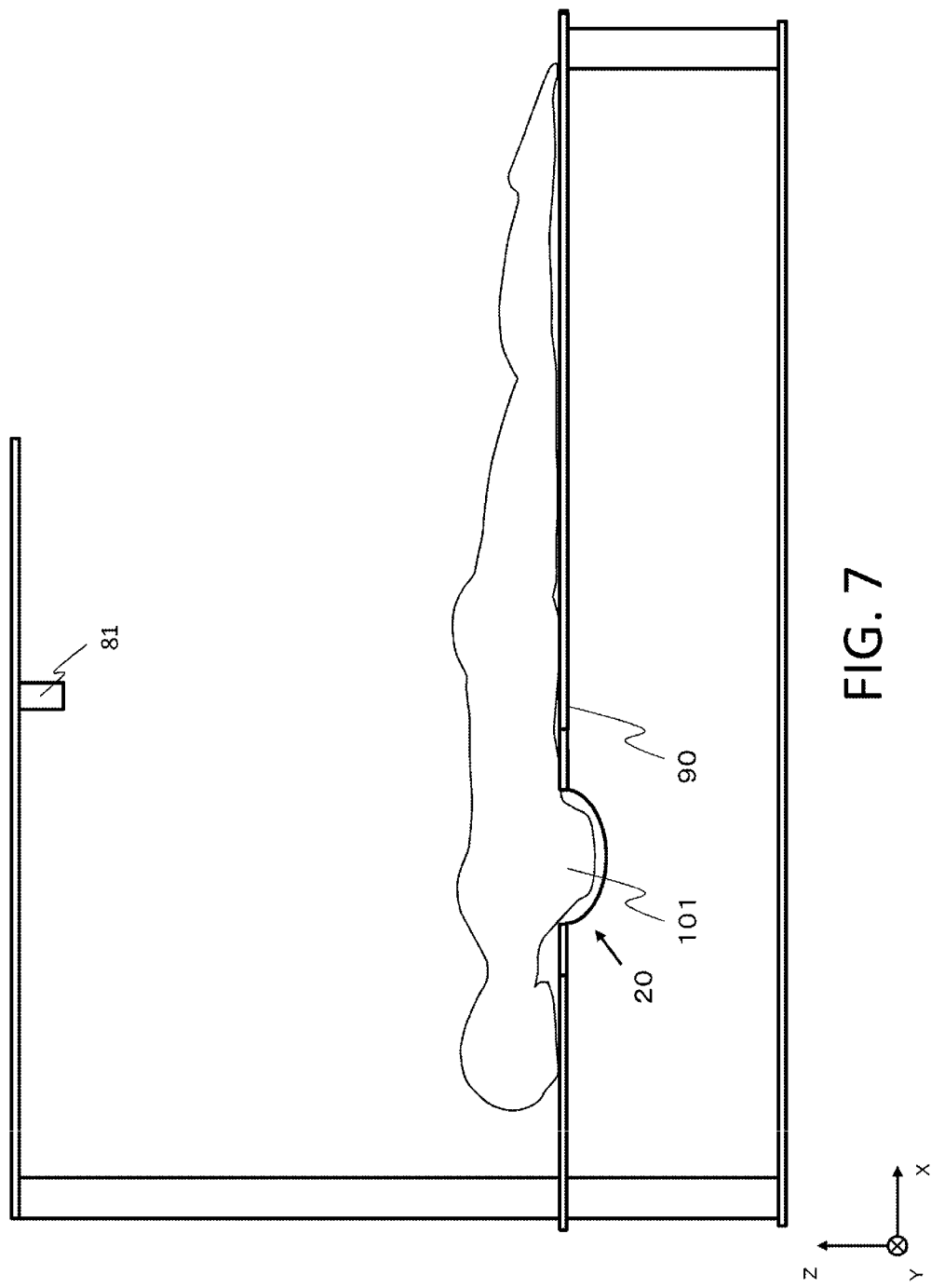
FIG. 7 is a diagram for describing a posture of an examinee.

As shown in FIG. 7, the photoacoustic measurement apparatus according to the embodiment performs measurement in a state in which an examinee in a prone position puts the breast in an opening provided at a housing 90.

The object holding unit 20 is a unit that holds an object inserted in the opening provided at the housing 90. In the embodiment, the object holding unit 20 has a holding member 21 having a circular bowl shape, a ring-shaped frame member 22 attached to the outer edge of the holding member 21, and a rubber member 23 that connects the frame member 22 and the housing 90 to each other.

In addition, the holding member 21 is configured to be movable three-dimensionally in the X, Y, and Z directions of FIG. 7 based on an instruction from the position control unit 60 that will be described later. That is, the holding member 21 is capable of varying a relative position with respect to the housing 90 with the expansion/contraction of the rubber member 23. In the embodiment, it is possible to adjust the contact state between an object and the holding member by the three-dimensional movement of the holding member 21.

The holding member 21 is preferably a member having high light transmittance in order to allow the transmission of light to be irradiated onto an object. In addition, it is preferable to use a material having acoustic impedance close to that of an object in order to allow the transmission of photoacoustic waves from the inside of the object. Such a material includes polymethylpentene, polyester, or the like.

«Probe Unit 30»

The probe unit 30 (corresponding to a measurement unit in the present invention) is a unit that receives acoustic waves generated inside an object and converts the received acoustic waves into an electric signal, and is a member having a plurality of acoustic elements arranged at its front surface. The acoustic elements are also called probes, acoustic wave probes, acoustic wave detectors, acoustic wave receivers, or transducers.

Since acoustic waves generated from a living body are ultrasonic waves in the range of 100 KHz to 100 MHz, elements capable of receiving the above frequency band are used as the acoustic elements provided in the probe unit 30. Specifically, it is possible to use transducers using a photoelectric phenomenon, transducers using the resonance of light, transducers using a change in capacity, or the like.

In addition, the acoustic elements desirably have high sensitivity and a wide frequency band. Specifically, the acoustic elements include piezoelectric elements made of, e.g., lead zirconate titanate (PZT), capacitive micromachined ultrasonic transducer (CMUT), elements using a Fabry-Perot Interferometer, or the like. However, besides the above acoustic elements, any acoustic element may be used so long as it satisfies the function of a probe.

In the embodiment, the probe unit 30 has a hemispherical shape as shown in FIG. 1 and has a plurality of acoustic elements arranged at its front surface (on the inner surface of its hemisphere). Since the probe unit 30 simultaneously receives acoustic waves at a plurality of positions, it is allowed to shorten a measurement time and reduce an influence due to the vibration of an object or the like. The position and direction of the acoustic elements are preferably adjusted such that the photoacoustic elements are allowed to efficiently receive photoacoustic waves generated from an object.

In addition, the probe unit 30 has, at its bottom part, the opening to allow the transmission of pulsed light emitted from the light irradiation unit 10.

In addition, the probe unit 30 is configured to be movable in a plane (in the X and Y directions of FIG. 1) perpendicular to a direction in which an object is inserted, based on an instruction from the position control unit 60 that will be described later. With this configuration, the probe unit 30 is allowed to receive acoustic waves at a plurality of mutually different positions with respect to an object and allowed to accurately acquire information. Note that the end of the irradiation optical system from which pulsed light is emitted and the probe unit 30 are preferably configured to move in synchronization with each other. In addition, an amplifier that amplifies an analog signal output from the acoustic elements may be provided inside the probe unit 30.

Note that the probe unit 30 may be a hand-held-type probe gripped and operated by a user. In addition, the acoustic elements may be arranged in an array called a 1-D array, a 1.5-D array, a 1.75-D array, or a 2-D array. Moreover, when the present invention is applied to a photoacoustic microscope, the probe unit 30 is preferably a focus-type probe and mechanically movable along the front surface of an object.

«Signal Processing Unit 40 and Display Control Unit 70»

The signal processing unit 40 is a unit that amplifies an acquired electric signal to be converted into a digital signal and generates distribution data on light absorption characteristics inside an object.

The signal processing unit 40 may be constituted by a circuit generally called a data acquisition system (DAS) and a processor such as a CPU, a MPU, and a GPU. In addition, the signal processing unit 40 may be constituted by an amplifier that amplifies a reception signal, an A/D converter that converts an analog reception signal into a digital signal, a memory such as a FIFO and a RAM that store a reception signal, an arithmetic circuit such as a FPGA chip. Moreover, the signal processing unit 40 may be constituted by a plurality of processors or arithmetic circuits.

Further, the signal processing unit 40 may be provided with a memory that stores a reception signal. The memory is typically constituted by a storage medium such as a ROM, a RAM, and a hard disk. Note that the memory may be constituted by a plurality of storage media. For example, the memory may be constituted by storage media such as one or more ROMs, RAMs, or hard disks.

The display control unit 70 corresponds to an image provision unit in the present invention, i.e., a unit that generates an image to be presented to a user based on data generated by the signal processing unit 40. Specifically, the display control unit 70 performs the generation of an image showing object information and the processing of a generated image (i.e., brightness conversion, distortion correction, and logarithmic compression processing, or the like). In addition, the display control unit 70 performs processing to arrange a plurality of generated images or display items in parallel to generate a user interface screen, or the like.

Figure 2:
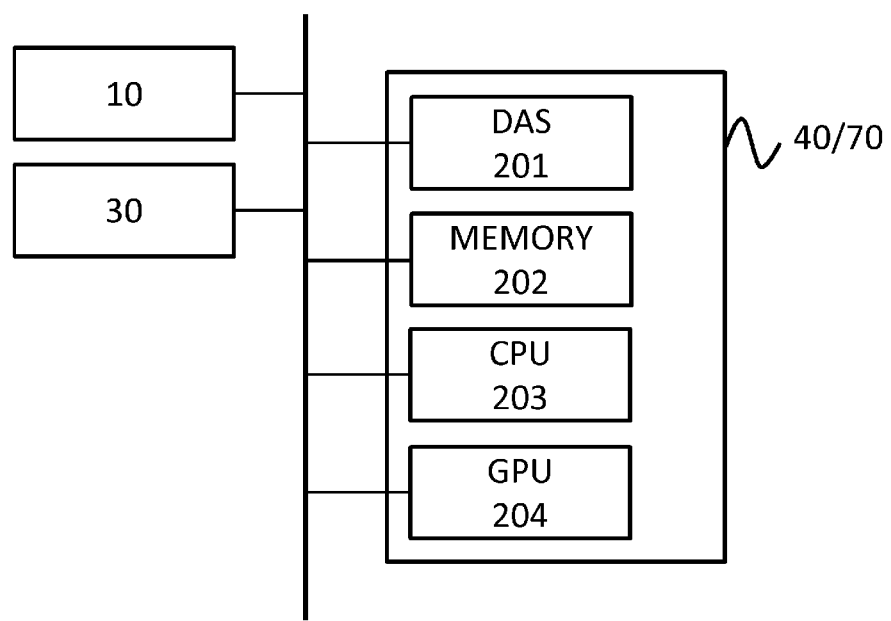
FIG. 2 is a diagram for describing the configurations of a signal processing unit and a display control unit.

FIG. 2 is a diagram showing a configuration example of the signal processing unit 40 in the embodiment. In the embodiment, the signal processing unit 40 has a DAS 201, a memory 202, a CPU 203, and a GPU 204. Note that in the embodiment, the signal processing unit 40 and the display control unit 70 that will be described later are implemented by the same hardware.

The DAS 201 is a unit that collects signals from a plurality of acoustic elements provided at the probe unit 30. Digital signals collected by the DAS 201 are stored in the memory 202.

The CPU 203 is a unit responsible for controlling the signal processing unit 40 and the display control unit 70. For example, the CPU 203 performs, with respect to digital signals stored in the memory 202, signal processing such as integration processing and correction processing, writing back of processed digital signals into the memory 202, the control of the GPU 204, or the like.

The GPU 204 is a unit that generates characteristics distribution data based on processed digital signals written in the memory 202. In addition, the GPU 204 is also a unit that performs, with respect to generated characteristics distribution data, various processing such as brightness conversion, distortion correction, and cutting out of an observation region to generate image data. Note that both the CPU 203 and the GPU 204 are used in the embodiment, but only the CPU 203 is used to perform the same processing.

«Recording Unit 100»

The recording unit 100 is a unit that retains a state of an object when measurement is performed, or measurement conditions (corresponding to history information in claims). For example, the recording unit 100 stores and retains the coordinates of a feature point obtained after the adjustment of a contact state, information showing a position of the holding member 21 (or the probe unit 30) after the adjustment, and an object image taken by a camera. Besides, the recording unit 100 may store data showing a shape of an object, data showing a posture of an examinee, or the like.

In addition, in the embodiment, the position control unit 60 has the function of automatically adjusting a position of the holding member 21 based on information recorded on the recording unit 100. Moreover, the display control unit 70 has the function of presenting information recorded on the recording unit 100 to a user. For example, the display control unit 70 displays an object image obtained at measurement in the past and a current object image in parallel. The processing will be described in detail later.

«Object 101»

An object 101 does not constitute a part of the photoacoustic measurement apparatus in the present invention but will be described below. The photoacoustic measurement apparatus according to the embodiment is mainly directed at photographing blood vessels, analyzing cancers or vascular diseases in persons or animals, monitoring chemical treatment over time, or the like. A light absorber inside an object is one having a relatively large absorption coefficient although it depends on light to be used. Specifically, the light absorber includes water, fat, protein, oxygenated hemoglobin, reduced hemoglobin, or the like.

«State Measurement Unit 50»

The state measurement unit 50 corresponds to a position acquisition unit in the present invention, i.e., a unit that acquires positional information on a predetermined region on an inserted object. In the embodiment, the state measurement unit 50 is provided at the bottom part of the probe unit 30 at which the irradiation of pulsed light is not hindered. The state measurement unit 50 takes an image of an object using an RGB camera, detects a papilla from the acquired image, and outputs the coordinates of the papilla together with the taken image.

Note that the state measurement unit 50 outputs the coordinates of a point showing a papilla in the embodiment, but may output coordinates corresponding to the feature point of a region other than the papilla (for example, a marker affixed to an object). In addition, an output target is not limited to a feature point, but the state measurement unit 50 may output information showing a position of a region on an object.

Moreover, the state measurement unit 50 may use a distance sensor or the like instead of a camera so long as the distance sensor is capable of acquiring information on a position of an inserted object. Position information and an image acquired by the state measurement unit 50 are transmitted to the position control unit 60 that will be described later for the adjustment of a position of the holding member 21.

«Position Control Unit 60»

The position control unit 60 is a unit that controls positions of the holding member 21 and the probe unit 30. Specifically, the position control unit 60 controls a position of the holding member 21 to adjust the contact state between an object and the holding member, and controls a position of the probe unit 30 to scan the object. The specific method of the processing will be described later.

«Display Unit 80»

The display unit 80 is a unit that displays an image, and is a display unit such as a liquid crystal, a CRT and an organic EL display. Note that the display unit 80 is not a requisite configuration for an object information acquisition apparatus according to the present invention.

<Method for Adjusting Contact State>

Next, a description will be given of a method for adjusting the contact state between an inserted object and the holding member with reference to FIGS. 3A, 3B and 4.

Figure 3A:
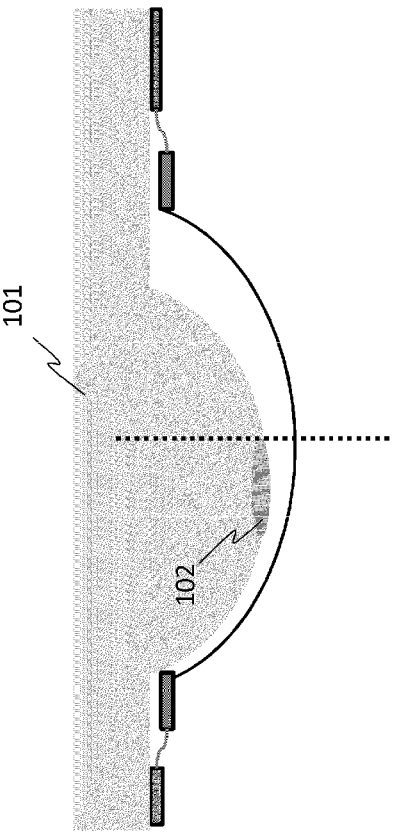
FIGS. 3A and 3B are diagrams for describing the contact state between an object and a holding member.
Figure 4:
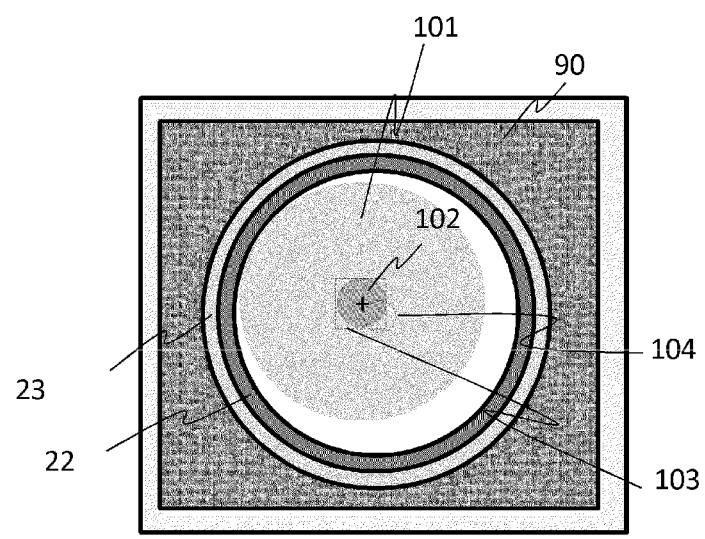
FIG. 4 is a diagram showing an example of an image generated by the display control unit.

FIG. 3A is a diagram showing a state in which an object 101 is inserted in the apparatus. As is clear from FIG. 3A, a papilla 102 is in a state of deviating from the center (dotted lines) of the holding member 21. When the object 101 (breast) comes in contact with the holding member in this state, the object and the holding member closely adhere to each other on the left side of FIG. 3A while a gap is produced between the object and the holding member on the right side of FIG. 3A. That is, since the characteristics of the propagation path of acoustic waves do not become uniform, the accuracy of acquired object information reduces.

Figure 3B:
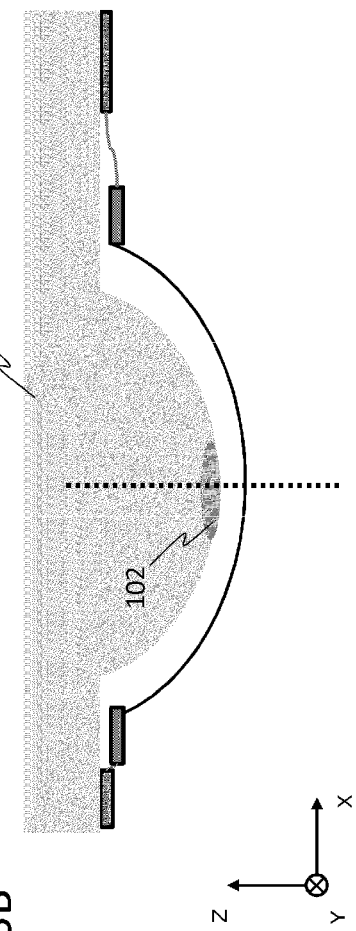

In such a case, the photoacoustic measurement apparatus according to the embodiment moves the holding member 21 using the position control unit 60 to correct the state into a state as shown in FIG. 3B. Thus, it is possible to make the contact state between the object and the holding member uniform.

A method for determining a movement amount and a movement direction of the holding member 21 will be described.

First, the apparatus measures a position of an object using the state measurement unit 50. For example, the measurement of a position may start with a user's input as a trigger, or may start when a pressure sensor provided in the object holding unit (for example, the ring-shaped frame member 22) detects a predetermined weight. Alternatively, the measurement may start when it is detected that the movement of the object stops after images of the object are continuously taken.

In addition, as described above, the state measurement unit 50 transmits, after acquiring an image of the object (hereinafter called an object image) and then acquiring the coordinates of the papilla based on the object image, the acquired coordinates to the display control unit 70 together with the object image.

Next, the display control unit 70 generates a screen to be presented to a user, based on the acquired coordinates and the object image. FIG. 4 is a diagram showing an example of the screen generated by the display control unit 70. The display control unit 70 superimposes a marker showing the papilla on the acquired object image to generate an image showing the positional relationship between the holding member 21 and the object and outputs the generated image to the display unit 80. Note that a rectangle indicated by symbol 103 is a graphic showing a position of the papilla detected by the state measurement unit 50 (+ mark inside the rectangle shows the center of the papilla). In addition, the display control unit 70 superimposes a marker showing the central point of the holding member 21 on the image. A region indicated by symbol 104 is the central point of the holding member.

Note that the information and the image are periodically updated. That is, on the screen, the papilla is in a state of being tracked in real time. Note that FIG. 4 shows the two-dimensional data, but three-dimensional data may be displayed when the state measurement unit 50 is capable of acquiring data in a depth direction with a distance sensor.

Note that the detection of the papilla by the state measurement unit 50 may be performed according to a known method. For example, an image of the papilla may be stored in advance to perform the detection based on pattern matching or the like. In addition, the state measurement unit 50 may not necessarily track the papilla, but a tracking target may be selected by the user. For example, an image acquired by a camera may be presented to the user via the display unit 80 to cause the user to specify a region (hereinafter called a feature point) as a tracking target via an input unit not shown. The feature point may be, for example, a papilla or a seal-shaped marker or may be any structure.

Next, a method for moving the object holding unit 20 with the position control unit 60 based on information (coordinates of the papilla) acquired by the state measurement unit 50 will be described.

The position control unit 60 determines whether the coordinates of the acquired feature point are included in a region in which the feature point is expected to be included at the start of measurement (hereinafter called a measurement start allowing region). For example, in the example of FIG. 4, the position control unit 60 determines whether the + mark showing the center of the papilla is placed inside the region 104. Note that the measurement start allowing region may be a three-dimensional region or a two-dimensional region.

Note that the state measurement unit 50 acquires the coordinates of the feature point in the embodiment but a target to be acquired by the state measurement unit 50 is not limited to a point. For example, the state measurement unit 50 may acquire positional information on a predetermined region on an object. In this case, a positive determination may be made when the region is completely included in the measurement start allowing region, or may be made when the region is partially included in the measurement allowing region.

Here, it is assumed that the measurement start allowing region is a circular region having a radius of 2 cm from the center of the holding member 21, and a determination is made as to whether the central coordinates of the papilla are included in the two-dimensional measurement start allowing region.

Here, when the central coordinates of the papilla are included in the measurement start allowing region, pulsed light is irradiated from the light source after the probe unit 30 has been moved to an appropriate position and then measurement starts. On the other hand, when the central coordinates of the papilla are not included in the measurement start allowing region, the holding member 21 is moved according to the following method.

First, the holding member 21 is temporarily moved in a direction in which the holding member 21 separates from the object (i.e., in a negative Z-axis direction). Then, the holding member 21 is moved in the X-Y plane. Finally, the holding member 21 is moved in a direction in which the holding member 21 gets close to the object again (i.e., in a positive Z-axis direction). Thus, it is possible to adjust the contact state without making the examinee uncomfortable. Note that the holding member 21 may be freely moved three-dimensionally so long as the examinee is free from uncomfortable feelings such as a pain.

Note that when the central coordinates of the papilla do not reach the inside of the measurement start allowing region even after the movement of the holding member 21, the user may be notified of the fact or the measurement may start after the central coordinates are moved to a position closest to the measurement start allowing region.

<Method for Measuring Object>

Figure 5:
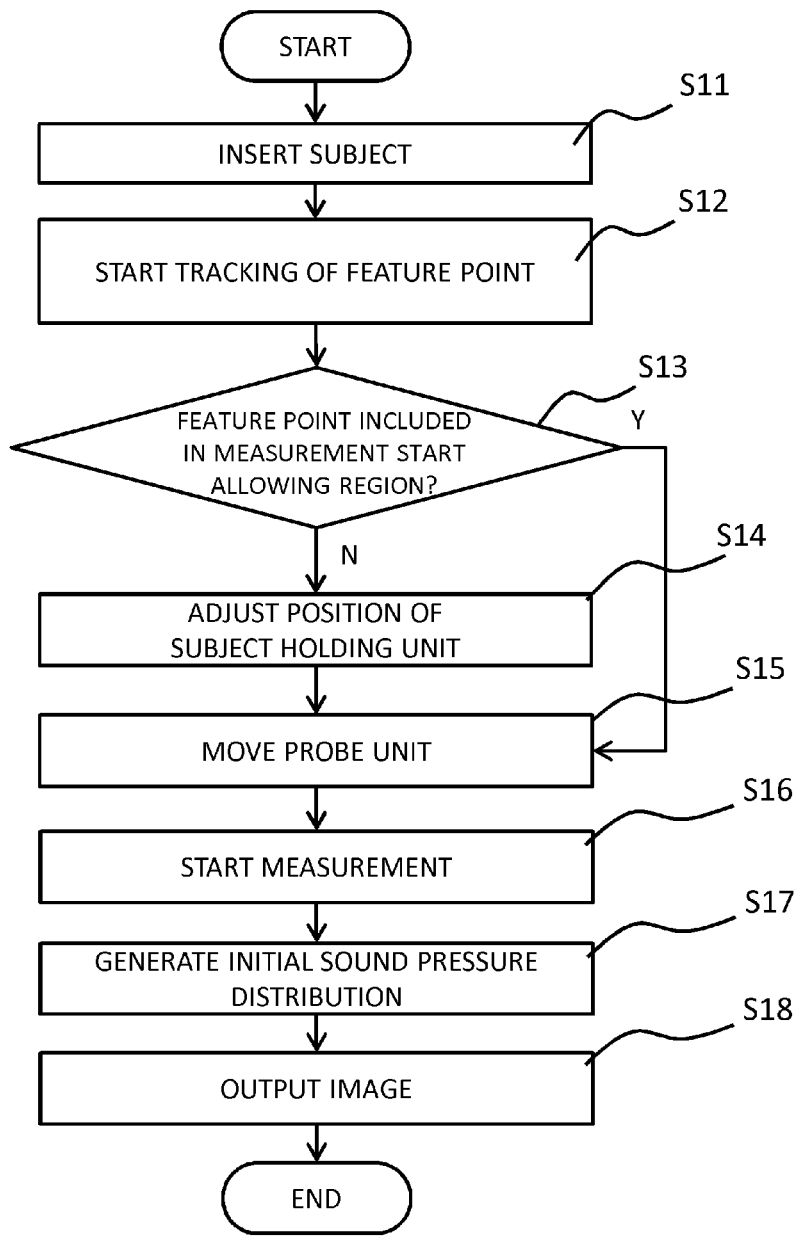
FIG. 5 is a measurement flowchart by a photoacoustic measurement apparatus according to the first embodiment.

Next, a description will be given, with reference to the flowchart of FIG. 5, of a method for measuring the breast serving as an object with the photoacoustic measurement apparatus according to the embodiment.

First, in step S11, an object is inserted in the insertion opening provided at the housing of the apparatus to come in contact with the holding member 21.

Next, in step S12, the tracking of a feature point (papilla) on the object starts. The tracking may start with the output of a pressure sensor or the like as a trigger or may start according to a user's operation.

Then, in step S13, a determination is made as to whether the feature point (the center of the papilla) is included in a measurement start allowing region. As a result, the processing transits to step S15 when a positive determination is made, and transits to step S14 when a negative determination is made.

In step S14, a position of the holding member 21 is moved via the position control unit 60. Note that a necessary movement amount may be calculated to move the holding member 21 at a time, or the processing may transit to step S13 every time the holding member 21 moves for a certain period of time or moves by a certain distance to periodically determine whether conditions are satisfied. In any case, the processing transits to step S15 when the feature point reaches the inside of the measurement start allowing region.

In step S15, the probe unit 30 is moved to an appropriate position according to a position of the object holding unit 20. Next, in step S16, the measurement of the object starts.

The method for measuring the object will be described.

First, pulsed light emitted from the light irradiation unit 10 is irradiated onto the object. The pulsed light is irradiated onto the object via a light propagation member (not shown) such as fibers and a lens at different times. The irradiated light propagates through and spreads into the object to be absorbed by a substance existing inside the object. When some of the energy of light propagating through the inside of a living body is absorbed by a light absorber such as blood, acoustic waves are generated from the light absorber due to thermal expansion. When a cancer exists inside the living body, the light is specifically absorbed by the new blood vessels of the cancer just like blood at other normal regions, whereby acoustic waves are generated.

That is, first photoacoustic waves are generated by the light irradiated at a first time, and second photoacoustic waves are generated by the light irradiated at a second time. The generated photoacoustic waves propagate through the inside of the object and reach the probes. Note that the probes are provided so as to acoustically match the object.

Each of the plurality of probes outputs a time-series signal with the reception of the photoacoustic waves. That is, the probes output a first time-series signal with the reception of the first photoacoustic waves, and output a second time-series signal with the reception of the second photoacoustic waves. The output signals are input to the signal processing unit 40.

The photoacoustic measurement apparatus according to the embodiment irradiates the pulsed light and receives the photoacoustic waves while shifting a position of the probe unit 30. That is, the signals corresponding to a plurality of positions are successively input to the signal processing unit 40.

Then, the signal processing unit 40 generates distribution such as characteristics distribution, concentration-related distribution, or the like based on the light absorption inside the object using the input signals, and outputs the generated distribution to the display control unit 70 (step S17).

Here, an example of calculating initial sound pressure distribution as an example of characteristics distribution based on light absorption will be described. An absorption coefficient $\mu_a$ at a certain position (i, j, k) inside an object may be calculated according to the following formula (1). Note that each of i, j, and k is an integer indicating coordinates inside the object. In addition, P indicates initial sound pressure (generated sound pressure) at the position (i, j, k), Γ indicates a Grueneisen constant, and φ indicates a light amount reaching the position (i, j, k).

$$P = \Gamma \cdot \mu_a \cdot \phi \qquad \text{Formula (1)}$$

Initial sound pressure P at the position (i, j, k) on a three-dimensional space coordinate system is calculated in such a way that signals output from probes for each channel are subjected to a band correction filter to be reconfigured.

As a reconfiguration method, a known method such as universal back projection (UBP) and filtered back projection (FBP) is available. In addition, Delay and Sum processing may be used.

By the application of the reconfiguration processing to each position inside the object, it is possible to calculate initial sound pressure at the position and acquire initial sound pressure distribution. Note that the initial sound pressure distribution may be three-dimensional distribution data (aggregate data of voxels) corresponding to a certain region inside the object or may be two-dimensional distribution data (aggregate data of pixels) corresponding to one cross-section of the three-dimensional distribution data.

<Adjustment of Contact State Using History Information>

Next, a description will be given of a specific method for bringing measurement conditions in the past close to current measurement conditions in the embodiment. In the embodiment, at the first measurement (after the adjustment of the contact state is finished), coordinates of a feature point, positional information on the holding member 21, and an object image taken by a camera provided in the state measurement unit 50 are stored in the recording unit 100. Then, at the second and subsequent measurement, the position control unit 60 moves the holding member 21 to the same position as the position at the previous measurement, based on the information stored in the recording unit 100 before the object is inserted (before step S11).

Figure 6:
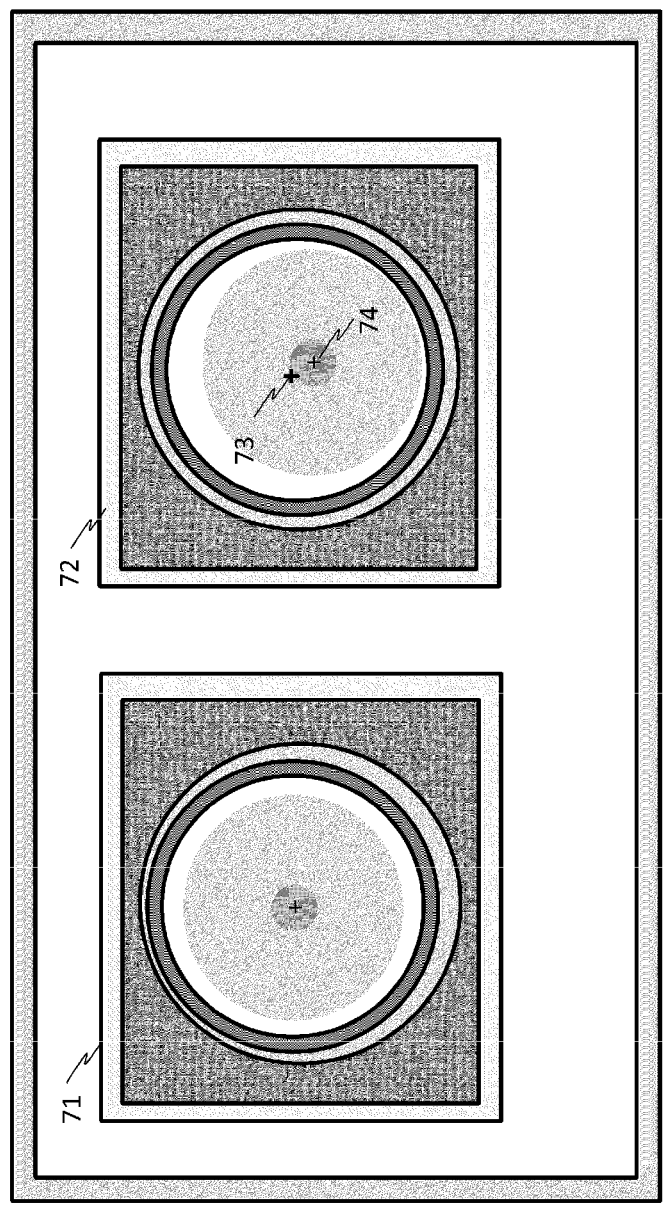
FIG. 6 is a diagram showing an example of a screen presented to a user in the first embodiment.

After the movement is finished, the object is inserted. On this occasion, the display control unit 70 generates as shown in FIG. 6 an image in which an object image (indicated by symbol 71) obtained at the previous measurement and a current object image (indicated by symbol 72) are arranged side by side, and outputs the generated image via the display unit 80. Note that symbol 73 indicates a marker showing the coordinates of the papilla obtained at the previous measurement and symbol 74 indicates a marker showing a current position of the papilla.

In the embodiment, it is possible to compare a state of an object obtained at previous measurement with a current state of the object in the way described above. Note that readjustment may be performed when the difference between a state of an object obtained at previous measurement and a current state of the object is detected. For example, a determination may be made as to whether the feature point (indicated by symbol 74) on the object is positioned near the feature point (indicated by symbol 73) obtained at the previous measurement. Based on this determination result, a screen display may be performed or the propriety of measurement may be determined.

As described above, in the first embodiment, it is possible to record in advance information on a state of an object obtained at previous measurement (i.e., the state of the object after the adjustment of a contact state) and then adjust the contact state between the object and the holding member at the second and subsequent measurement using the information. In addition, by presenting an image in which object images are displayed side by side to a user, it is possible to bring a state of an object close to a state of the object obtained at previous measurement.

Note that a position of a feature point on an object may be acquired using the state measurement unit 50 after the object is inserted to determine whether the feature point is included in a measurement start allowing region. When the feature point is not included in the measurement start allowing region, a position of the holding member 21 may be adjusted again.

Note that when the present invention is applied to a photoacoustic microscope of a light focus type or a photoacoustic microscope of an acoustic focus type using a focus type probe, distribution data may be generated without performing reconstruction processing. Specifically, the probe unit 30 and the end of the irradiation optical system are moved relative to the object 101 by a scanning mechanism (not shown), and photoacoustic waves are received at a plurality of scanning positions. Then, after obtained reception signals are subjected to envelop detection with respect to a change in time, a time-axis direction is converted into a depth direction in a signal for each light pulse and plotted on a space coordinate system. By performing this processing for each scanning position, it is possible to configure distribution data.

Note that when initial sound pressure distribution calculated in the way described above is corrected by the distribution of the amounts of light reaching the inside of an object, absorption coefficient distribution may be calculated. The distribution of the amounts of light reaching the inside of an object may be calculated using, for example, the distribution of the amounts of the light irradiated onto the object and light propagation characteristics inside the object. On this occasion, a shape of the object may be taken into consideration.

Further, in a case in which a positional deviation or deformation occurs between a plurality of characteristics distribution at the same position when light having a single wavelength is irradiated or occurs between characteristics distribution at the same position when light having a plurality of wavelengths is irradiated, the alignment between the plurality of characteristics distribution or the like may be performed. It is possible to perform the alignment according to a known method such as affine transformation and free form deformation (FFD).

Generated data is converted into image data showing characteristics information (for example, initial sound pressure distribution or absorption coefficient distribution) inside a living body and output via the display unit 80 (step S18). An image may be, for example, three-dimensional data or two-dimensional data.

<First Example>

Next, a description will be given of a specific example of the photoacoustic measurement apparatus according to the first embodiment.

In the example, a breast-simulating phantom was used as the object. In addition, a cup-shaped member made of polymethylpentene was used as the holding member. Moreover, a plurality of conversion elements having frequency band characteristics of 2 MHz±70% was arranged on the hemispherical probe unit.

In the example, first, the breast-simulating phantom was relatively fixed with respect to the housing. On this occasion, a marker was affixed onto a position corresponding to the papilla of the phantom, and the phantom was mounted in a state of deviating by 3 cm in direct distance from the central point of the holding member 21 within a plane parallel to the housing 90.

The state measurement unit 50 is provided at the lowermost point of the probe unit 30, and has a configuration by which it is possible to confirm the positional relationships between the object 101, the holding member 21 and its surrounding members, and the housing 90 via the display unit 80.

In the example, a user set the marker affixed onto the phantom as a tracking target via a user interface provided in the display unit. In addition, in the example, the inside of a circular region having a radius of 1 cm from the center of the holding member was set as a measurement start allowing region.

In the above state, since the tracking target was not included in the measurement start allowing region, the holding member 21 was moved. Note that the coordinates of the tracking target were defined and calculated using coordinates within the plane parallel to the housing with a certain point on the housing as an origin. In addition, the coordinates of the measurement start allowing region were calculated using the coordinates within the plane parallel to the housing based on the frame member 22.

In the movement of the holding member 21, first of all the holding member 21 was temporarily moved in a direction separating from the phantom. Specifically, the holding member 21 was moved in the negative Z-axis direction until the pressure sensor provided in the frame member 22 was not allowed to detect pressure. After that, the holding member 21 was moved within the XY plane until the coordinates of the marker entered the measurement start allowing region. Specifically, the holding member 21 was moved until the coordinates of the marker entered a circular region having a radius of 0.5 cm from the center of the measurement start allowing region. Then, the holding member 21 was moved in the positive Z-axis direction to finish its holding operation.

Next, after the probe unit 30 was moved by the same amount as that of the holding member 21 to perform the processing of step S13 again, measurement was started.

In the step of measuring the object, pulsed light having a wavelength of 797 nm was irradiated from the light source, and photoacoustic waves were received by the acoustic elements. In addition, image reconfiguration was performed using universal back projection based on received signals to obtain three-dimensional initial sound pressure distribution.

The obtained initial sound pressure distribution was three-dimensional image data having 160 voxels in length, 160 voxels in width, and 200 voxels in height. In addition, light amount distribution was corrected with respect to the obtained initial sound pressure distribution to calculate absorption coefficient distribution.

According to the above example, even when the marker-affixed point of the breast phantom was deviated from the measurement start allowing region, it was confirmed that the measurement was allowed without moving the phantom.

As described above, in the first embodiment, the unit that holds an object (the object holding unit 20) and the unit that measures the object (the probe unit 30) are configured to be separately movable. Thus, even if the contact state between an inserted object and the holding member is not preferable, it is possible to adjust the contact state without moving the object, improve the accuracy of measurement, and easily bring current measurement conditions close to measurement conditions in the past.

(Second Embodiment)

A second embodiment refers to an embodiment in which information on a posture of an examinee obtained at previous measurement is recorded in advance besides information on a state of the object obtained at the previous measurement as in the first embodiment and the information is presented to a user at the next and subsequent measurement.

As shown in FIG. 7, a photoacoustic measurement apparatus according to the second embodiment differs from the photoacoustic measurement apparatus according to the first embodiment in that it further has a sensor 81 provided upward in the vertical direction of an examinee and detecting a position of the body of the examinee.

The sensor 81 is a unit (a depth sensor) that takes an image of an examinee from above and acquires a depth image. Note that any sensor other than a depth sensor may be used so long as it is capable of acquiring information on a posture of an examinee.

In addition, in the second embodiment, the display control unit 70 has the function of estimating the bone of an examinee based on the output of the sensor 81 and outputting an image via the display unit 80. For example, the display control unit 70 outputs an image obtained by adding an image showing a skeletal state of an examinee to an object image.

In the second embodiment, at the first measurement (after the adjustment of a contact state is finished), the coordinates of a feature point, positional information on a holding member 21, an object image taken by a camera provided in a state measurement unit 50, and positional information on the bone of an examinee are stored in the recording unit 100.

Then, at the second and subsequent measurement, a position control unit 60 moves, just like the first embodiment, the holding member 21 to the same position as a position at the previous measurement, based on information stored in the recording unit 100.

After the movement is finished, an object is inserted. On this occasion, as shown in FIG. 8, the display control unit 70 generates an image in which a current object image and an object image obtained at the previous measurement are arranged parallel to their corresponding images showing the states of the bones (hereinafter called skeletal states), and outputs the generated image via the display unit 80.

Figure 8:
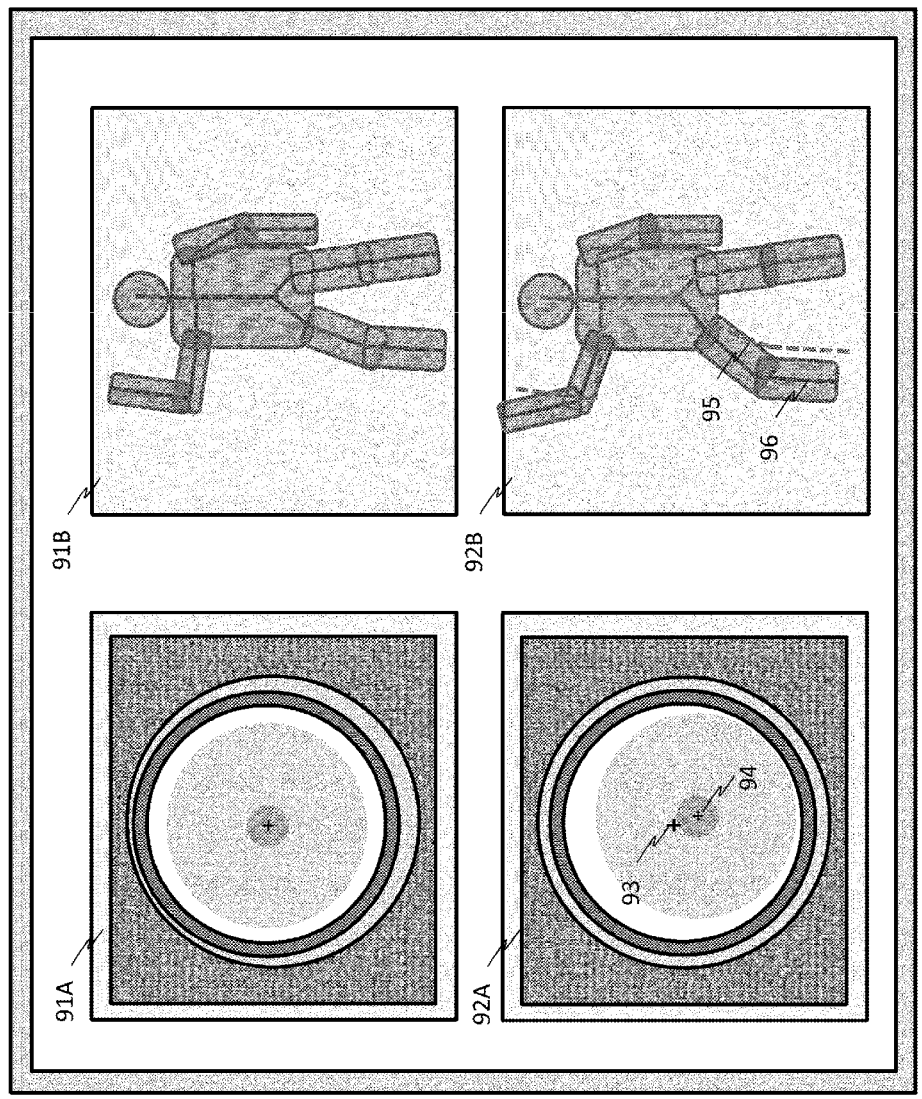
FIG. 8 is a diagram showing an example of a screen presented to a user in a second embodiment.

In FIG. 8, symbol 91A indicates the object image obtained at the previous measurement, and symbol 91B indicates the image showing the skeletal state (hereinafter called the bone image) obtained at the previous measurement. In addition, symbol 92A indicates the current object image, and the symbol 92B indicates a current bone image. Symbol 93 is a marker showing the coordinates of a papilla obtained at the previous measurement, and symbol 94 is a marker showing a current position of the papilla.

Note that in the example, the bone image obtained at the previous measurement is superimposed on the current bone image. For example, symbol 95 indicates a position of the bone of the right leg obtained at the previous measurement, and symbol 96 indicates a current position of the bone of the right leg.

As described above, an image showing a skeletal state of an examinee is further output in the second embodiment. Therefore, it is possible to compare a skeletal state obtained at previous measurement with a current skeletal state and cause the examinee to take a similar posture. That is, it is possible to bring a state of an inserted object close to a previous measurement state of the object.

Note that a bone is estimated in the embodiment but any information other than a skeletal state may be presented so long as it is capable of presenting a posture of an examinee. For example, an image of an examinee taken by a camera may be presented.

In addition, in the example of FIG. 8, the two sets of the information (91A and 91B) obtained at the previous measurement and the current information (92A and 92B) are displayed in parallel. However, both the information (91A and 91B) obtained at previous measurement and the current information (92A and 92B) may be each superimposed to display only one set of the images. On this occasion, in order to allow the distinction between the information obtained at the previous measurement and the current information, the feature points or the bones may be decorated. For example, the feature points or the bones may be decorated by colors, patterns (a solid line and dotted lines, lighting and blinking, or the like), or the like. In addition, a display to evaluate the deviation amounts between both the information may be output. Thus, it is possible for a user to determine whether an object state is close to a state obtained at previous measurement.

(Third Embodiment)

A third embodiment refers to an object information acquisition apparatus that processes a hand as an object.

A photoacoustic measurement apparatus according to the third embodiment differs from those of the first and second embodiments in that it uses a plane-shaped member instead of a hemispherical member as an object holding unit 20.

In the third embodiment, light is irradiated onto an object via an opening, and a probe unit 30 receives photoacoustic waves. The probe unit 30 in the third embodiment is a hemispherical array having a plurality of conversion elements having a frequency band of 2 MHz±70%. The other configurations of the third embodiment are the same as those of the first embodiment.

In the first and second embodiments, the object holding unit 20 is moved to adjust the contact state between the object holding unit and an object. On the other hand, in the third embodiment, the object holding unit 20 is moved to adjust the relative position between an object and the probe unit.

When it is not possible to reproduce a position of an object obtained at previous measurement due to the deviation of the mounting position of the object, the object holding unit is moved within a movable region to adjust a position of the object in the embodiment.

The embodiment will be described with reference to FIGS. 9A to 9E.

Symbol 1 indicates the photoacoustic measurement apparatus, symbol 20 indicates the plane-shaped object holding unit, symbol 20A indicates the movable region of the object holding unit 20, and the symbol 101 indicates an object. In addition, symbol 20B indicates the object holding unit 20 after being moved.

Figure 9A:
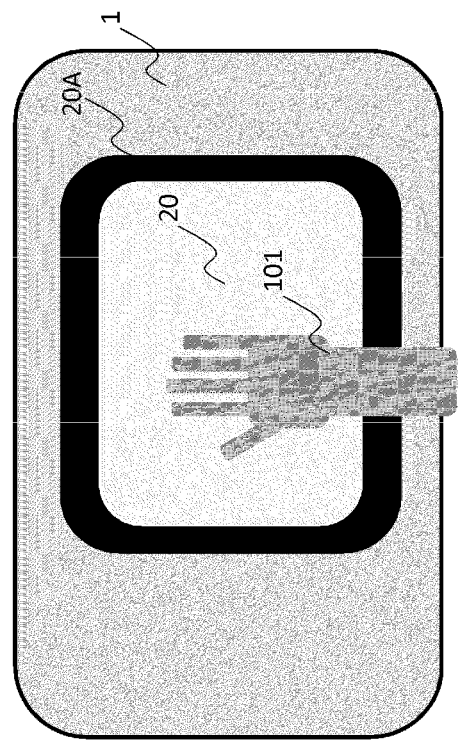
FIGS. 9A to 9E are diagrams for describing a third embodiment.
Figure 9B:
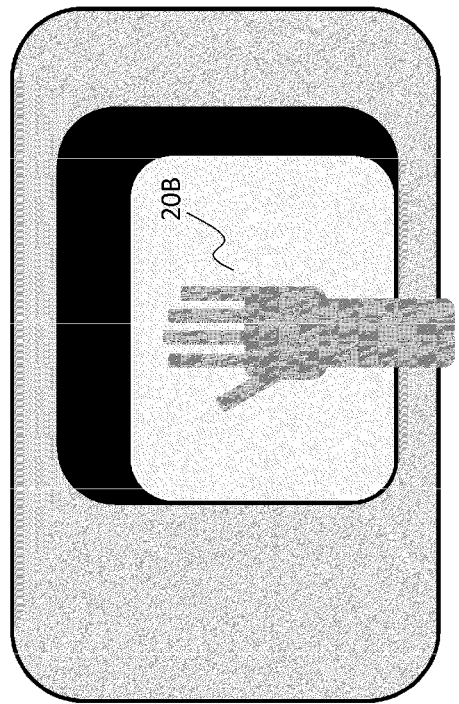
Figure 9C:
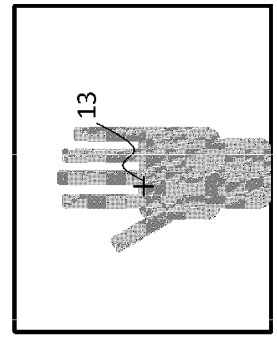
Figure 9D:
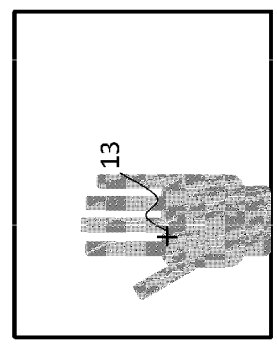
Figure 9E:
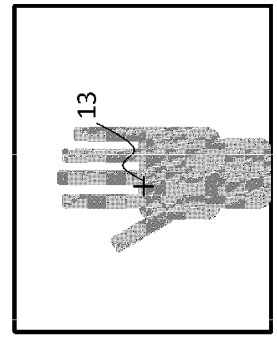

Moreover, FIG. 9C is an image of the object (hereinafter called a camera image) taken at the previous measurement. Further, symbol 11 indicates a feature point set at the previous measurement, and symbol 12 indicates an object region. FIG. 9D shows a current camera image. Furthermore, symbol 13 is a feature point set at this measurement. Furthermore, FIG. 9E shows a camera image taken after the movement of the object holding unit 20.

In the embodiment, a state measurement unit 50 has a camera, and acquires and stores a camera image every time measurement is performed.

Note that a user specifies a feature point in the example, but the apparatus may automatically extract a feature point according to an object. For example, a corresponding feature point may be extracted according to a known technology such as SIFT and SURF.

In addition, each region of a living body may be recognized according to a known technology. For example, a region to be desirably measured may be specified to automatically extract a feature point.

First, an examinee puts the object 101.

Next, the user of the apparatus sets a point corresponding to the feature point 11 on the currently-displayed camera image by referring to the camera image obtained at the previous measurement (symbol 13).

Then, the position control unit moves the object holding unit 20 such that the coordinates of the feature points match each other. Note that even if the deviation between the coordinates of the feature points does not get close to zero after the movement of the object holding unit, the object holding unit is moved such that the deviation between the coordinates of the feature points becomes minimum.

The calculation of the deviation between the coordinates of the feature points is desirably performed after the movement of the object holding unit. However, a movement destination of the object holding unit may be determined in advance such that the distance between the feature points becomes minimum to move the object holding unit. That is, in this case, it is not necessary to measure the deviation again. For example, with a threshold (3 mm, 5 mm, or the like) provided based on an allowable error, it is possible to determine that the deviation gets close to zero when the deviation is less than or equal to the threshold, and then finish the movement.

After the movement is finished, it becomes possible to press a measurement button on an interface screen. When the user presses the measurement button, measurement starts.

Next, pulsed light having a wavelength of 797 nm is irradiated onto the object from the light irradiation unit 10, and photoacoustic waves are received by the probe unit 30. Then, a signal processing unit 40 performs image reconfiguration using universal back projection method based on obtained reception signals. Thus, three-dimensional initial sound pressure distribution is obtained. In the example, data having 160 voxels in length, 160 voxels in width, and 200 voxels in height is obtained as the initial sound pressure distribution. In addition, by the correction of the light amount distribution of the obtained initial sound pressure distribution, it is possible to calculate absorption coefficient distribution.

In the third embodiment, when the coordinates of feature points do not completely match each other, measurement is performed after an object is moved to a position at which the coordinates are as close as possible to each other. Additionally, a deviation degree is also presented to the user of the apparatus.

Figure 10A:
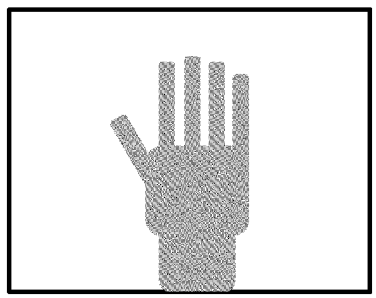
FIGS. 10A and 10B are diagrams for describing the third embodiment.
Figure 10B:
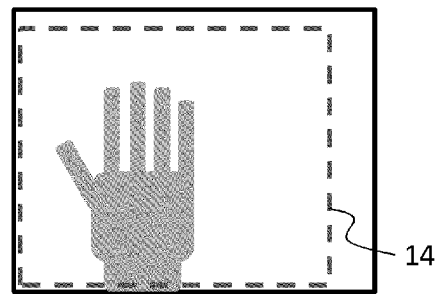

FIG. 10A shows an example of a camera image taken at previous measurement, and FIG. 10B shows an example of a camera image taken at this measurement. Symbol 14 indicates a region corresponding to the camera image taken at the previous measurement. Thus, when a positional deviation of an object is not completely corrected, the deviation may be visually displayed.

Note that when a corresponding region is calculated between a camera image taken at previous measurement and a camera image taken at this measurement, the following methods are available. For example, there is a method in which a correlation in a superimposed region is calculated while two images are relatively deviated from each other to calculate a parallel movement amount.

Besides parallel movement, deformation alignment according to a known technology such as FFD may be performed to calculate a deformation amount or a movement amount of a corresponding image.

In addition, when the coordinates of a corresponding feature point between a camera image taken at previous measurement and a camera image taken at this measurement are revealed, it is possible to present a corresponding region without calculating correlation or the like.

For example, a measurement region at this measurement may be calculated based on the relationship between the coordinates of a feature point and a measurement region obtained at previous measurement, and then displayed in a camera image taken at this measurement. Thus, it is possible to show a corresponding region between two images to be easily understandable.

Moreover, in this example, the parallel movement amount between the two images is calculated. However, a rotation amount may be simultaneously calculated. Further, the object holding unit 20 may be configured to be rotatable such that an object is rotated based on a calculated rotation amount to perform alignment.

(Fourth Embodiment)

A fourth embodiment refers to an object information acquisition apparatus that processes a hand as an object just like the third embodiment. However, the fourth embodiment differs from the third embodiment in that a feature point is not strictly aligned but measurement starts when the feature point is included inside a measurement region.

A description of the embodiment will be given with reference to FIGS. 11A to 11D. Note that the same configurations as those of the third embodiment will be denoted by the same symbols and their descriptions will be omitted.

Figure 11B:
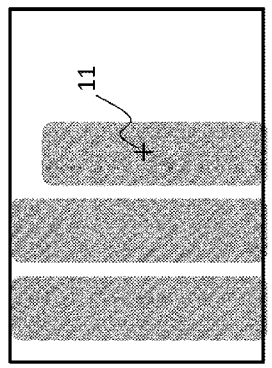
FIGS. 11A to 11D are diagrams for describing a fourth embodiment.

FIG. 11B shows a camera image obtained at previous measurement. In addition, symbol 11 indicates a feature point set at the previous measurement.

Figure 11C:
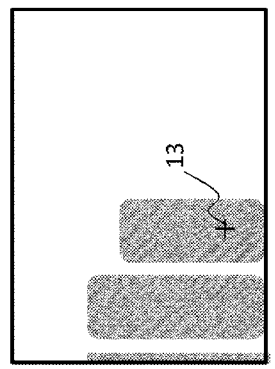

FIG. 11C shows a current camera image. In addition, symbol 13 indicates a feature point set at this measurement.

Figure 11D:
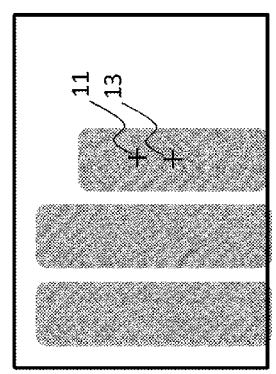
Figure 11A:
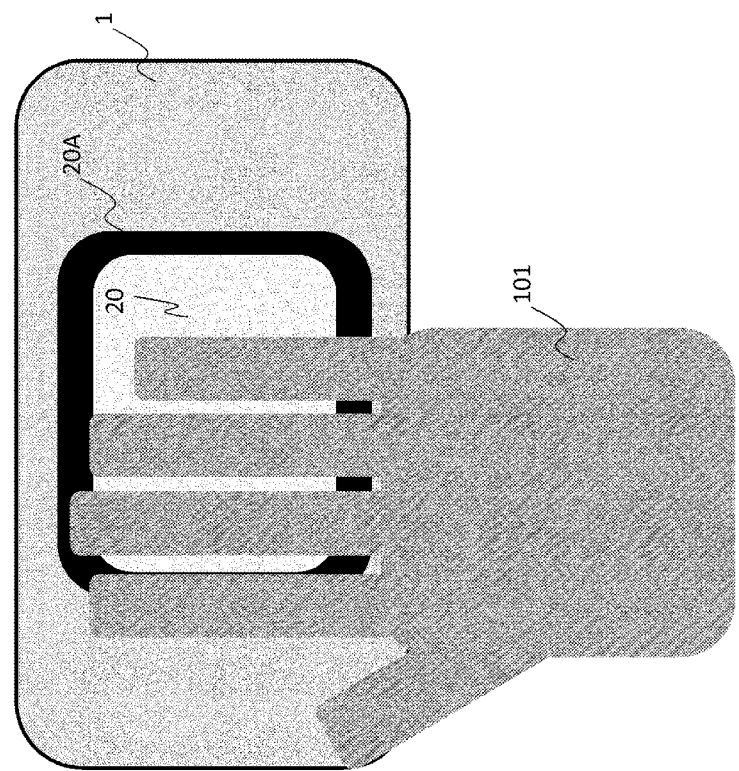

Moreover, FIG. 11D shows a camera image obtained when an object holding unit is moved.

As is clear from FIG. 11D, the position of the feature point obtained at the previous measurement and the position of the feature point obtained at this measurement are different. However, both the feature points exist inside a measurement region.

In the fourth embodiment, in such a case, it is determined that the measurement of an object can be performed, and control for allowing the start of the measurement is performed. Note that in the fourth embodiment, processing for visually displaying the corresponding relationship between a camera image taken at previous measurement and a camera image taken at this measurement is not performed.

Since the other processing is the same as that of the third embodiment, their descriptions will be omitted.

(Fifth Embodiment)

A fifth embodiment refers to an embodiment in which an object is aligned according to a result obtained when measurement is performed using a modality other than a photoacoustic measurement apparatus.

A photoacoustic measurement apparatus according to the fifth embodiment acquires an object image (or a camera image) acquired by another X-ray diagnostic apparatus and then moves an object holding unit 20 based on the image. Thus, it is possible to generate an object image at almost the same position region as that of the image generated by the X-ray diagnostic apparatus.

Figure 12A:
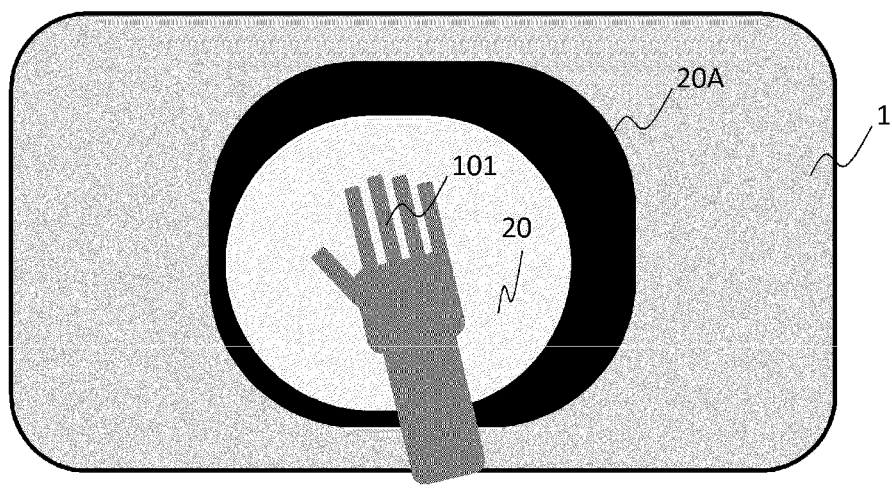
FIGS. 12A to 12C are diagrams for describing a fifth embodiment.

A description of a specific operation will be given with reference to FIGS. 12A to 12C. Note that the same configurations as those of the third embodiment will be denoted by the same symbols and their descriptions will be omitted.

Figure 12B:
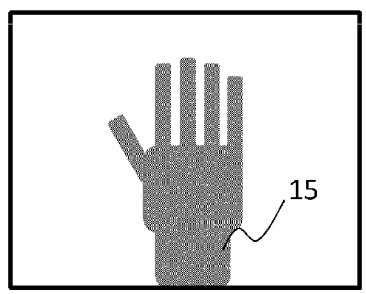

FIG. 12B shows a camera image acquired by an X-ray diagnostic apparatus. In addition, symbol 15 denotes a position of an object obtained when an image is taken using the X-ray diagnostic apparatus.

Figure 12C:
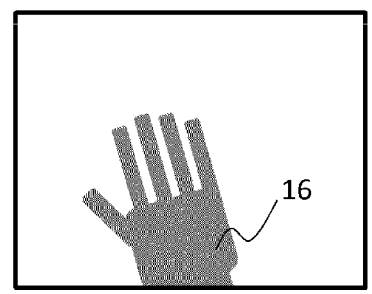

FIG. 12C shows a camera image acquired by the photoacoustic measurement apparatus. In addition, symbol 16 indicates a current position of the object.

In the fifth embodiment, the matrix of rotation and translation movement is calculated based on a plurality of feature points existing in an image to find a movement amount of an object. The extraction of the feature amounts and the calculation of the matrix are desirably performed according to a known image processing method. For example, it is possible to extract the feature points using SIFT or SURF and calculate the corresponding relationship between the feature points according to a method such as RANSAC.

In addition, after the calculation of the corresponding relationship between the plurality of feature points, the matrix of the rotation and the translation movement between the corresponding feature points are calculated according to a least squares method or the like.

Then, a movement amount is calculated based on the calculated matrix of the rotation and the translation movement to rotate and translationally move the object holding unit 20.

Note that after the movement of the object holding unit, the same process of calculating a movement amount may be repeatedly performed a plurality of times. Thus, it is possible to correct a deviation of the object more accurately.

After the movement is finished, it becomes possible to press a measurement bottom on an interface screen. When a user presses the measurement bottom, measurement starts.

According to the fifth embodiment, since it is possible to align an object based on an image acquired by another object information acquisition apparatus, the comparison between mutual images is facilitated.

Note that although images acquired by cameras installed in both modalities are used to calculate a movement amount in the embodiment, the movement amount may be calculated based on a result obtained when the images are subjected to image processing. In addition, a movement amount may be calculated based on acquired object images (for example, X-ray images) rather than camera images.

(Modified Example)

Note that each of the embodiments is only for illustration purpose for describing the present invention and the present invention may be carried out by the modifications or combinations of the embodiments in an appropriate fashion without departing from its scope.

For example, the present invention may be carried out as an object information acquisition apparatus including at least some of the above means. In addition, the present invention may be carried out as a method for controlling the object information acquisition apparatus. The above processing and means may be freely combined together to be carried out so long as no technological contradictions arise.

Moreover, in each of the embodiments, one RGB camera provided at the bottom of the probe unit 30 is used as the state measurement unit 50. However, another means may be used to acquire information on a position of an object. For example, a plurality of RGB cameras may be fixed to the apparatus independently of the probe unit 30 to three-dimensionally detect a position of a feature point. Further, a distance sensor may be used to acquire a position or a shape of a feature point. Furthermore, these means may be used in combination with the above sensor 81.

Furthermore, an image taking range of the camera and an image taking range (measurement range) of the apparatus match each other in each of the descriptions of the embodiments, but they may not necessarily match each other.

Furthermore, in each of the third to fifth embodiments, a position of the object is adjusted by the movement of the object holding unit. However, when the unit (probe unit) that performs the measurement is movable, both the object holding unit and the measurement unit may be moved. Furthermore, only the measurement unit may be moved.

Furthermore, in each of the first and second embodiments, the holding member 21 is held by the ring-shaped frame member 22 and the rubber member 23. However, any configuration for holding the holding member 21 is available so long as it is capable of moving the holding member 21. For example, the frame member 22 may be omitted, or a frame member having another shape may be used. Furthermore, only the frame member 22 may be used without the holding member 21. In this case, since it becomes possible to insert, by the movement of the frame member 22, an object (for example, the breast) in the opening of the housing without causing an examinee to move on the housing 90, a burden on the examinee (the burden of aligning a position at measurement) is reduced.

Furthermore, in each of the embodiments, the plurality of acoustic elements is arranged in the probe unit 30. However, when the present invention is applied to a device such as a photoacoustic microscope that processes a relatively small object as an examination target, one acoustic element may be used. Note that when the present invention is applied to an apparatus that processes a relatively large object such as the breast as an examination target, a plurality of acoustic elements is preferably used.

Furthermore, in each of the first and second embodiments, the holding member 21 is caused to come in contact with the object again to adjust the contact state. However, the object may be moved in a state in which the holding member comes in contact with the object.

Furthermore, in each of the embodiments, the description is given using the apparatus that measures the object based on a photoacoustic effect as an example. However, it is also possible to apply the present invention to another modality so long as it is an apparatus that acquires object information based on acoustic waves from the inside of the object. For example, it is also possible to apply the present invention to a measurement apparatus that uses ultrasonic echoes or a measurement apparatus based on diffused light tomography.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-168247, filed on Aug. 27, 2015, and Japanese Patent Application No. 2016-146655, filed on Jul. 26, 2016, which are hereby incorporated by reference herein in their entirety.

What is claimed is:

1. An object information acquisition apparatus comprising:
   a holding member configured to come in contact with an inserted object to hold the inserted object and to be movable relative to the inserted object;
   a measurement unit configured to receive acoustic waves from an inside of the inserted object and to be movable relative to the inserted object; and
   a computer configured to function as a position control unit which controls a position of the holding member, to adjust a contact state between the inserted object and the holding member, and which controls a position of the measurement unit,
   wherein the position control unit controls the position of the holding member independently of the position of the measurement unit, and
   wherein the position control unit is configured to adjust the contact state between the holding member and the inserted object when the contact state and history information on the contact state is compared and found to be different, the history information having been obtained in a previous measurement of the inserted object.

2. The object information acquisition apparatus according to claim 1, wherein the measurement unit is configured to receive the acoustic waves from the inside of the inserted object via the holding member.

3. The object information acquisition apparatus according to claim 1, further comprising a position acquisition unit configured to acquire positional information corresponding to a predetermined region or point on the inserted object,
   wherein the position control unit is configured to adjust the contact state between the holding member and the inserted object based on the positional information.

4. The object information acquisition apparatus according to claim 3, wherein the holding member has a hemispherical shape,
   the position acquisition unit is configured to acquire positional information corresponding to a papilla, and
   the position control unit is configured to control the position of the holding member so that the papilla is at a bottom of the holding member.

5. The object information acquisition apparatus according to claim 3, wherein the position acquisition unit is configured to acquire the positional information corresponding to the region or the point on the inserted object, the positional information being specified by a user.

6. The object information acquisition apparatus according to claim 1, wherein the measurement unit is configured to be movable along a first plane perpendicular to a direction in which the inserted object is inserted, and
   the holding member is configured to be movable along the direction in which the inserted object is inserted, besides the first plane.

7. The object information acquisition apparatus according to claim 6, wherein, when adjusting the state of contact between the holding member and the inserted object, the position control unit is configured to move the holding member in a direction in which the holding member separates from the inserted object, then move the holding member along the first plane, and thereafter move the holding member in a direction in which the holding member comes in contact with the inserted object again.

8. The object information acquisition apparatus according to claim 1, further comprising:
   a display controller configured to acquire an image of the inserted object and present the acquired image to a user.

9. The object information acquisition apparatus according to claim 8, wherein the display controller is configured to simultaneously present to the user the contact state and the history information on the contact state.

10. The object information acquisition apparatus according to claim 8, wherein the history information includes at least one of positional information used when the contact state between the inserted object and the holding member is adjusted, information on a position of the holding member after adjustment, an image of the inserted object, and information on a posture of an examinee.

11. The object information acquisition apparatus according to claim 1, further comprising:
    an information acquisition unit configured to acquire information on the inside of the inserted object based on acoustic waves received by the measurement unit.

12. The object information acquisition apparatus according to claim 1, further comprising:
    a storage unit configured to store the history information.

13. An object information acquisition apparatus comprising:
    a measurement unit configured to receive acoustic waves from an inside of an object;
    a holding member configured to come in contact with the object to hold the object and to be movable relative to the measurement unit; and
    a computer configured to function as a position control unit which controls a position of the holding member to adjust the position of the object,
    wherein the position control unit is configured to adjust a position of the object relative to the measurement unit, when the position of the object is compared with and found to be different from history information on a position of the object relative to the measurement unit obtained during a previous measurement of the object.

14. The object information acquisition apparatus according to claim 13, wherein the position control unit is configured to move the holding member such that a difference, between the position of the object relative to the measurement unit and the history information on a position of the object relative to the measurement unit, satisfies a predetermined condition.

15. The object information acquisition apparatus according to claim 13, further comprising:
    a display controller configured to generate and present an image showing a difference between a current measurement region of the object and a measurement region of the object obtained during a previous measurement of the object.

16. The object information acquisition apparatus according to claim 13, wherein the position control unit is configured to move the holding member such that a portion of the object where the object had been measured during the previous measurement lies within a measurable area, the measureable area being an area from which the acoustic waves therefrom can be received by the measurement unit.

17. The object information acquisition apparatus according to claim 13, wherein the history information is information generated by an apparatus configured to acquire information on the object by means, which is different from the object information acquisition apparatus.

18. The object information acquisition apparatus according to claim 13, further comprising:
an information acquisition unit configured to acquire information on the inside of the object based on acoustic waves received by the measurement unit.

19. The object information acquisition apparatus according to claim 13, further comprising:
a storage unit configured to store the history information.

* * * * *